United States Patent
Jung et al.

(10) Patent No.: US 10,105,118 B2
(45) Date of Patent: Oct. 23, 2018

(54) APPARATUS AND METHOD OF PROCESSING MEDICAL IMAGE

(71) Applicant: SAMSUNG ELECTRONICS CO., LTD., Suwon-si (KR)

(72) Inventors: Ji-young Jung, Bucheon-si (KR); Toshihiro Rifu, Suwon-si (KR); Gun-woo Lee, Seoul (KR); Jong-hyon Yi, Yongin-si (KR); Chang-lae Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 523 days.

(21) Appl. No.: 14/851,098

(22) Filed: Sep. 11, 2015

(65) Prior Publication Data
US 2016/0157812 A1    Jun. 9, 2016

(30) Foreign Application Priority Data
Dec. 3, 2014  (KR) .................. 10-2014-0172383

(51) Int. Cl.
*A61B 6/03*    (2006.01)
*A61B 6/00*    (2006.01)
(Continued)

(52) U.S. Cl.
CPC .............. *A61B 6/542* (2013.01); *A61B 6/032* (2013.01); *A61B 6/488* (2013.01); *A61B 6/5211* (2013.01);
(Continued)

(58) Field of Classification Search
CPC ......... A61B 6/032; A61B 6/488; A61B 6/542; H05G 1/30
See application file for complete search history.

(56) References Cited

U.S. PATENT DOCUMENTS

| | | | | | |
|---|---|---|---|---|---|
| 5,379,333 | A | * | 1/1995 | Toth | A61B 6/032 378/108 |
| 5,696,807 | A | * | 12/1997 | Hsieh | A61B 6/032 378/109 |

(Continued)

FOREIGN PATENT DOCUMENTS

| | | |
|---|---|---|
| JP | 2003-70921 A | 3/2003 |
| KR | 10-0830198 B1 | 5/2008 |

(Continued)

OTHER PUBLICATIONS

Communication dated Feb. 15, 2016, issued by the Korean Intellectual Property Office in corresponding Korean Application No. 10-2014-0172383.

(Continued)

*Primary Examiner* — Thomas R Artman
(74) *Attorney, Agent, or Firm* — Sughrue Mion, PLLC

(57) ABSTRACT

An apparatus and a method of processing a medical image are provided. The apparatus is configured to generate a cross-sectional image of an object by transmitting X-rays through a region of the object, and includes an X-ray generator configured to generate the X-rays. The apparatus further includes a controller configured to determine sub-regions included in the region, based on positions of body parts included in the region, determine image qualities of the sub-regions based on types of the body parts included in the sub-regions, control doses of the X-rays based on the image qualities, and control the X-ray generator to transmit the controlled X-rays to the region.

20 Claims, 16 Drawing Sheets

Priority table

| BODY PART | PRIORITY | IMAGE QUALITY INDEX |
|---|---|---|
| LIVER | 1 | 15 |
| PELVIS | 2 | 18 |
| LUNGS | 3 | 25 |
| BRAIN | 4 | 10 |

(51) Int. Cl.
*G06F 3/0484* (2013.01)
*A61B 6/02* (2006.01)

(52) U.S. Cl.
CPC .......... *G06F 3/04842* (2013.01); *A61B 6/027* (2013.01); *A61B 6/461* (2013.01)

(56) References Cited

U.S. PATENT DOCUMENTS

| | | | |
|---|---|---|---|
| 7,215,733 B2 | 5/2007 | Nabatame | |
| 7,587,023 B2 | 9/2009 | Hur | |
| 7,602,880 B2* | 10/2009 | Hirokawa | A61B 6/032 378/108 |
| 2009/0046833 A1* | 2/2009 | Hirokawa | A61B 6/032 378/108 |
| 2013/0051645 A1 | 2/2013 | Kim et al. | |
| 2014/0148690 A1 | 5/2014 | Kim et al. | |
| 2014/0328447 A1* | 11/2014 | Koweek | A61B 6/405 378/4 |

FOREIGN PATENT DOCUMENTS

| | | |
|---|---|---|
| KR | 10-2013-0023735 A | 3/2013 |
| KR | 10-2014-0067526 A | 6/2014 |

OTHER PUBLICATIONS

Communication dated Sep. 8, 2016, issued by the Korean Intellectual Property Office in counterpart Korean application No. 10-2014-0172383

* cited by examiner

Priority table

| BODY PART | PRIORITY | IMAGE QUALITY INDEX |
|---|---|---|
| LIVER | 1 | 15 |
| PELVIS | 2 | 18 |
| LUNGS | 3 | 25 |
| BRAIN | 4 | 10 |

APPARATUS AND METHOD OF PROCESSING MEDICAL IMAGE

CROSS-REFERENCE TO RELATED APPLICATION

This application claims priority from Korean Patent Application No. 10-2014-0172383, filed on Dec. 3, 2014, in the Korean Intellectual Property Office, the disclosure of which is incorporated herein by reference in its entirety.

BACKGROUND

1. Field

Apparatuses and methods consistent with exemplary embodiments relate to an apparatus and a method of processing a medical image.

2. Description of the Related Art

Tomography apparatuses are used to acquire images showing an internal structure of an object. The tomography apparatuses are non-invasive examination devices that capture and process images of details of structures, tissues, flow of fluid, etc., inside a body, and provide the images to a user. A user, e.g., a medical practitioner, may use images output from the tomography apparatuses to diagnose a patient's condition and diseases.

The user may adjust a resolution of a cross-sectional image obtained by tomography apparatuses. To do so, the user may control an amount of X-rays passing through an object. In this case, the user may consider several factors such as a penetration rate of X-rays irradiated onto a portion of the object and a thickness and a density of the portion.

SUMMARY

Exemplary embodiments address at least the above problems and/or disadvantages and other disadvantages not described above. Also, the exemplary embodiments are not required to overcome the disadvantages described above, and may not overcome any of the problems described above.

Exemplary embodiments provide an apparatus and a method of processing a medical image whereby an amount of X-rays to which a plurality of body parts are exposed may be reduced by taking into account a penetration rate of X-rays irradiated onto a portion, a thickness and a density of the portion, etc.

Exemplary embodiments provide an apparatus and a method of processing a medical image whereby an amount of X-rays to which an organ is exposed may be minimized by emitting X-rays according to priority among overlapping regions between a plurality of organs.

According to an aspect of an exemplary embodiment, there is provided a medical imaging apparatus a medical image processing apparatus configured to generate a cross-sectional image of an object by transmitting X-rays through a region of the object, the apparatus including an X-ray generator configured to generate the X-rays. The apparatus further includes a controller configured to determine sub-regions included in the region, based on positions of body parts included in the region, determine image qualities of the sub-regions based on types of the body parts included in the sub-regions, control doses of the X-rays based on the image qualities, and control the X-ray generator to transmit the controlled X-rays to the region.

In response to the sub-regions overlapping each other, the controller may be further configured to determine an image quality of an overlapping region between the sub-regions based on priorities of the body parts.

The image qualities may include image quality indices of the body parts, and each of the image quality indices may be determined based on a signal-to-noise ratio of a cross-sectional image showing a respective one of the body parts.

The apparatus may further include an interface configured to receive an input of priorities and/or image quality indices of the body parts.

The image qualities may include image quality indices of the body parts, and each of the image quality indices may be determined based on a density and/or a volume of a respective one of the body parts.

The X-ray generator may be further configured to transmit the X-rays through the object to generate a scout image for determining the positions of the body parts.

The apparatus may further include a display configured to display the scout image and/or the cross-sectional image.

The display may be further configured to display the scout image on which the positions of the body parts are indicated.

The scout image on which the positions of the body parts are indicated may be generated based on a reference image on which the positions of body parts are set.

The apparatus may further include an interface configured to receive an input for modifying the positions of the body parts that are indicated on the scout image.

The apparatus may further include an interface configured to receive an input for selecting the body parts.

The controller may be further configured to determine another region of the object to which the X-rays are transmitted, based on the selected body parts.

The controller may be further configured to control the doses of the X-rays that are transmitted to the respective sub-regions, based on the image qualities.

The apparatus may further include a display configured to display the controlled doses of the X-rays that are transmitted to the respective sub-regions.

The medical image processing apparatus may be a tomography apparatus, and the controller may be further configured to control a tube current per rotation of each of the X-rays that are transmitted to the respective sub-regions, based on the image qualities.

According to an aspect of another exemplary embodiment, there is provided a medical image processing method of generating a cross-sectional image of an object by transmitting X-rays through a region of the object, the method including generating the X-rays. The method further includes determining sub-regions included in the region, based on positions of body parts included in the region, determining image qualities of the sub-regions based on types of the body parts included in the sub-regions, controlling doses of the X-rays based on the image qualities, and transmitting the controlled X-rays to the region.

In response to the sub-regions overlapping each other, the determining the image qualities may include determining an image quality of an overlapping region between the sub-regions based on priorities of the body parts.

The controlling the doses of the X-rays may include controlling the doses of the X-rays that are transmitted to the respective sub-regions, based on the image qualities.

The method may further include displaying the controlled doses of the X-rays that are transmitted to the respective sub-regions.

According to an aspect of another exemplary embodiment, there is provided a medical image processing apparatus including an X-ray generator configured to generate an X-ray. The apparatus further includes a controller configured to determine a region of an object, the region including a body part, determine an image quality of the region based on a type of the body part, and control the X-ray generator to transmit a dose of the X-ray to the region based on the image quality.

The controller may be further configured to determine a priority and/or an index of the region based on a table including the type of the body part corresponding to the priority and/or the index, and control the X-ray generator to transmit a tube current per rotation of the X-ray to the region based on the priority and/or the index.

The X-ray generator may be further configured to generate another X-ray, and the controller may be further configured to determine another region of the object, the other region including another body part, determine another image quality of the other region based on another type of the other body part, and control the X-ray generator to transmit another dose of the other X-ray to the other region based on the other image quality.

BRIEF DESCRIPTION OF THE DRAWINGS

The above and/or other aspects will be more apparent by describing exemplary embodiments with reference to the accompanying drawings in which.

DETAILED DESCRIPTION OF THE EXEMPLARY EMBODIMENTS

Figure 1:
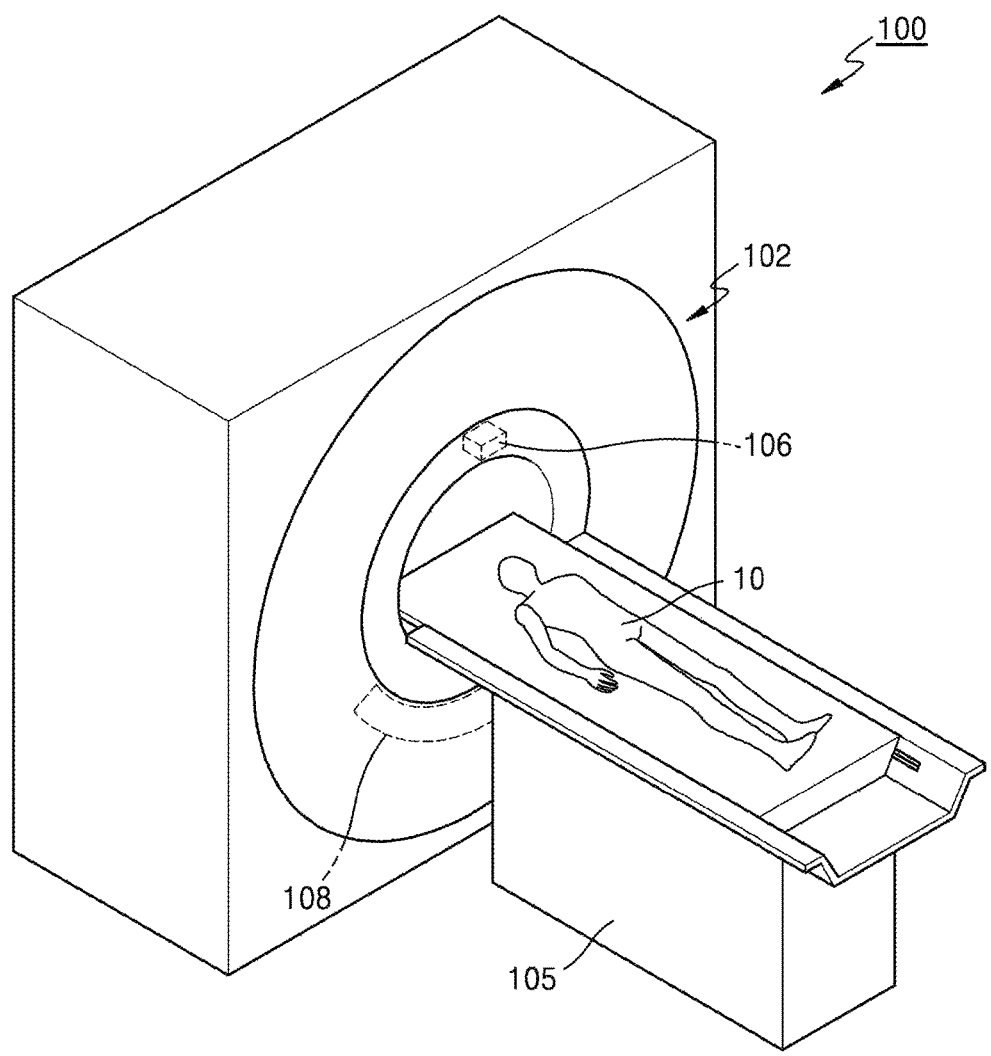
FIG. 1 is a view of a computed tomography (CT) system according to an exemplary embodiment.

Exemplary embodiments are described in greater detail herein with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those defined matters. Also, well-known functions or constructions are not described in detail since they would obscure the description with unnecessary detail.

All terms including descriptive or technical terms which are used herein should be construed as having meanings that are obvious to one of ordinary skill in the art. However, the terms may have different meanings according to the intention of one of ordinary skill in the art, precedent cases, or the appearance of new technologies. Also, some terms may be arbitrarily selected by the applicant, and in this case, the meaning of the selected terms will be described in detail in the detailed description of the exemplary embodiments.

It will be understood that the terms "comprises" and/or "comprising" used herein specify the presence of stated features or components, but do not preclude the presence or addition of one or more other features or components. In addition, the terms such as "unit," "-er (-or)," and "module" described in the specification refer to an element for performing at least one function or operation, and may be implemented in hardware, software, or the combination of hardware and software.

Throughout the specification, an "image" may mean multi-dimensional data formed of discrete image elements, e.g., pixels in a two-dimensional (2D) image and voxels in a three-dimensional (3D) image. For example, the image may include a medical image of an object, which is captured by a computed tomography (CT) imaging apparatus.

Throughout the specification, a "CT image" may mean an image generated by synthesizing a plurality of X-ray images that are obtained by photographing an object while a CT imaging apparatus rotates around at least one axis with respect to the object.

Throughout the specification, an "object" may be a human, an animal, or a portion of a human or animal. For example, the object may be an organ (e.g., the liver, heart, womb, brain, breast, or abdomen), a blood vessel, or a combination thereof. The object may be a phantom. The phantom may mean a material having a density, an effective atomic number, and a volume that are approximately the same as those of an organism. For example, the phantom may be a spherical phantom having properties similar to the physical body.

Throughout the specification, a "user" may be, but is not limited to, a medical expert including a medical doctor, a nurse, a medical laboratory technologist, a medical image expert, or a technician who repairs a medical apparatus.

Because a CT system is capable of providing a cross-sectional image of an object, the CT system may distinctively express an inner structure, e.g., an organ such as a kidney or a lung, of the object, compared to a general X-ray imaging apparatus.

The CT system may obtain a plurality of pieces of image data with a thickness not more than 2 mm several tens to several hundred times per second, and then may process the plurality of pieces of image data, so that the CT system may provide a relatively accurate cross-sectional image of the object. According to the related art, only a horizontal cross-sectional image of the object can be obtained, but this issue has been overcome due to various image reconstruction methods. Examples of 3D image reconstruction methods are as below:

Shade surface display (SSD)—an initial 3D imaging method of displaying only voxels having a predetermined Hounsfield Units (HU) value;

Maximum intensity projection (MIP)/minimum intensity projection (MinIP)—a 3D imaging method of displaying only voxels having the greatest or smallest HU value among voxels that construct an image;

Volume rendering (VR)—an imaging method capable of adjusting a color and transmittance of voxels that constitute an image, according to areas of interest;

Virtual endoscopy—a method that allows endoscopy observation in a 3D image that is reconstructed by using the VR method or the SSD method;

Multi-planar reformation (MPR)—a method of reconstructing an image into a different cross-sectional image, in which a user may reconstruct an image in any desired direction;

Editing—a method of editing adjacent voxels to allow a user to easily observe an area of interest in volume rendering; and Voxel of interest (VOI)—a method of displaying only a selected area in volume rendering.

FIG. 1 is a view of a CT system 100 according to an exemplary embodiment. Referring to FIG. 1, the CT system 100 includes a gantry 102, a table 105, an X-ray generator 106, and an X-ray detector 108.

The gantry 102 may include the X-ray generator 106 and the X-ray detector 108.

An object 10 is positioned on the table 105.

The table 105 may move in a predetermined direction (e.g., at least one of up, down, right, and left directions) during a CT imaging procedure. Also, the table 105 may tilt or rotate by a predetermined angle in a predetermined direction.

The gantry 102 may also tilt by a predetermined angle in a predetermined direction.

Figure 2:
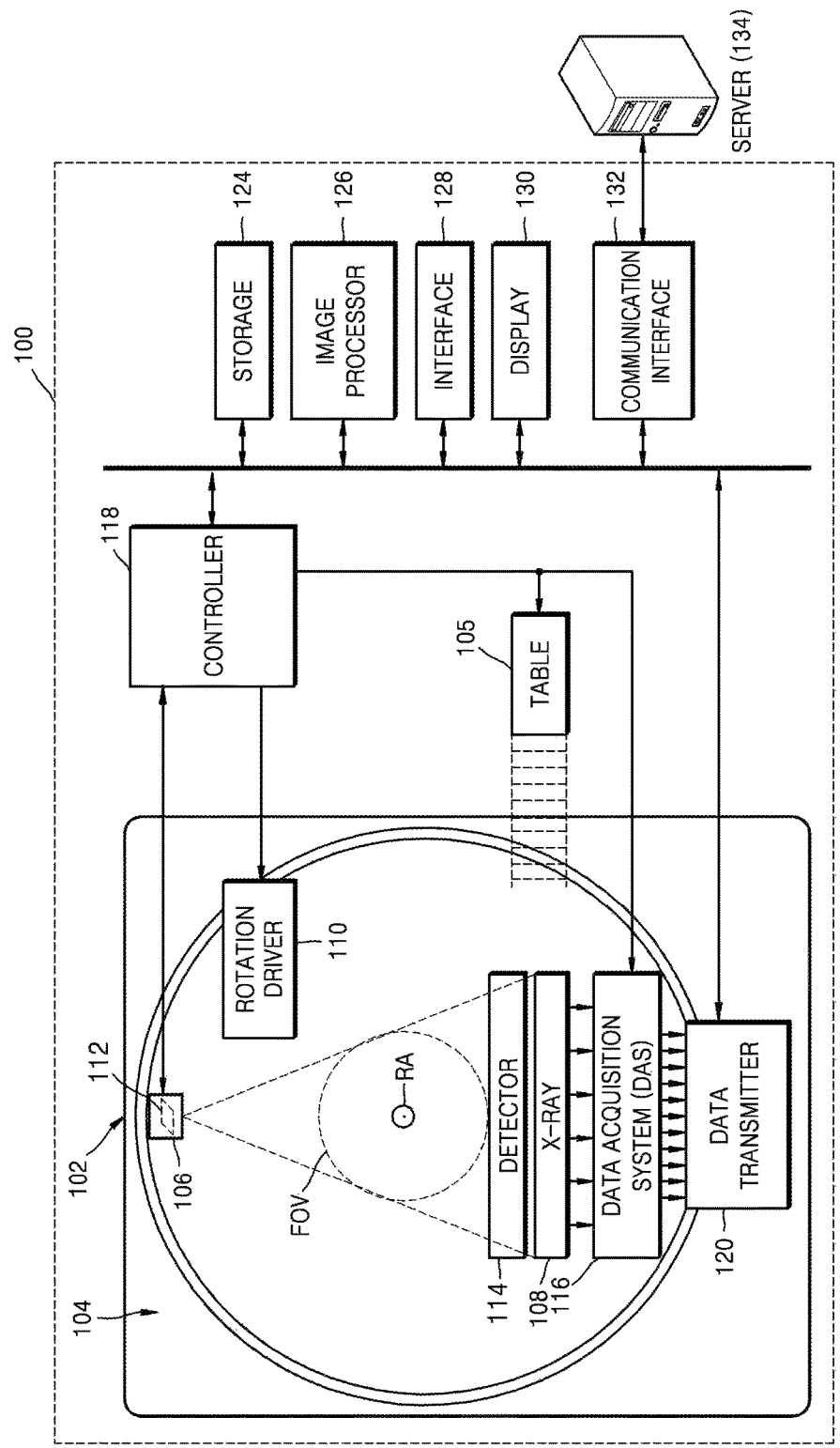
FIG. 2 is a schematic diagram of a CT system according to an exemplary embodiment.

FIG. 2 is a schematic diagram of the CT system 100. Referring to FIG. 2, the CT system 100 includes the gantry 102, the table 105, a controller 118, a storage 124, an image processor 126, an interface 128, a display 130, and a communication interface 132.

As described above, the object 10 is positioned on the table 105. The table 105 may move in a predetermined direction (e.g., at least one of up, down, right, and left directions), and movement of the table 105 may be controlled by the controller 118.

The gantry 102 includes a rotating frame 104, the X-ray generator 106, the X-ray detector 108, a rotation driver 110, a data acquisition system (DAS) 116, and a data transmitter 120.

The rotating frame 104 may have a loop shape capable of rotating with respect to a predetermined rotation axis RA. Also, the rotating frame 104 may have a disc shape.

The X-ray generator 106 and the X-ray detector 108 are arranged to face each other to have predetermined fields of view FOV. The rotating frame 104 also includes an anti-scatter grid 114. The anti-scatter grid 114 is positioned between the X-ray generator 106 and the X-ray detector 108.

In a medical imaging system, X-ray radiation that reaches a detector (or a photosensitive film) includes not only attenuated primary radiation that forms a valuable image but also scattered radiation that deteriorates the quality of an image. To transmit most of the primary radiation and to attenuate the scattered radiation, the anti-scatter grid 114 may be positioned between a patient and the detector (or the photosensitive film).

For example, the anti-scatter grid 114 may be formed by alternately stacking lead foil strips and an interspace material such as a solid polymer material, solid polymer, or a fiber composite material. However, formation of the anti-scatter grid 114 is not limited thereto.

The rotating frame 104 receives a driving signal from the rotation driver 110, and rotates the X-ray generator 106 and the X-ray detector 108 at a predetermined rotation speed. The rotating frame 104 may receive the driving signal and power from the rotation driver 110 while the rotating frame 104 contacts the rotation driver 110 via a slip ring. Also, the rotating frame 104 may receive the driving signal and power from the rotation driver 110 via wireless communication.

The X-ray generator 106 may receive a voltage and current from a power distribution unit (PDU) via a slip ring and then a high voltage generator, and generates and emits an X-ray. When the high voltage generator applies predetermined voltage (hereinafter, referred to as a tube voltage) to the X-ray generator 106, the X-ray generator 106 may generate X-rays having a plurality of energy spectra that correspond to the tube voltage.

The X-ray generated by the X-ray generator 106 is emitted in a predetermined form due to a collimator 112.

The X-ray detector 108 is positioned to face the X-ray generator 106. The X-ray detector 108 may include a plurality of X-ray detecting devices. Each of the plurality of X-ray detecting devices may establish one channel, but exemplary embodiments are not limited thereto. The X-ray detector 108 detects the X-ray that is generated by the X-ray generator 106 and that is transmitted through the object 10, and generates an electrical signal corresponding to an intensity of the detected X-ray.

The X-ray detector 108 may include an indirect-type X-ray detector for detecting radiation after converting the radiation into light, and a direct-type X-ray detector for detecting radiation after directly converting the radiation into electric charges. The indirect-type X-ray detector may use a scintillator. Also, the direct-type X-ray detector may use a photon counting detector. The DAS 116 is connected to the X-ray detector 108. Electrical signals generated by the X-ray detector 108 are acquired by the DAS 116. Also, the electrical signals generated by the X-ray detector 108 may be provided to an analog-to-digital converter via an amplifier.

According to a slice thickness or a number of slices, only some of a plurality of pieces of data collected by the X-ray detector 108 may be provided to the image processor 126 via the data transmitter 120, or the image processor 126 may select only some of the plurality of pieces of data.

Such a digital signal is provided to the image processor 126 via the data transmitter 120. The digital signal may be provided to the image processor 126 by wire or wirelessly.

The controller 118 may control an operation of each of the elements in the CT system 100. For example, the controller 118 may control operations of the table 105, the rotation driver 110, the collimator 112, the DAS 116, the storage 124, the image processor 126, the interface 128, the display 130, the communication interface 132, and the like.

The image processor 126 receives data acquired by the DAS 116 (e.g., raw data that is data before processing), via the data transmitter 120, and performs pre-processing. The pre-processing may include, for example, a process of correcting a sensitivity irregularity between channels, and a process of correcting signal loss due to a rapid decrease in signal strength or due to a presence of an X-ray absorbing material such as metal.

Data output from the image processor 126 may be referred to as raw data or projection data. The projection data may be stored in the storage 124 with imaging conditions (e.g., the tube voltage, an imaging angle, etc.) during the acquisition of data.

The projection data may be a group of data values that correspond to the intensity of the X-ray that has passed through the object 10. For convenience of description, a group of a plurality of pieces of projection data that are simultaneously obtained from all channels at the same imaging angle is referred to as a projection data set.

The storage 124 may include at least one storage medium among a flash memory-type storage medium, a hard disk-type storage medium, a multimedia card micro-type storage medium, card-type memories (e.g., an SD card, an XD memory, and the like), random access memory (RAM), static random access memory (SRAM), read-only memory (ROM), electrically erasable programmable ROM (EE-PROM), programmable ROM (PROM), magnetic memory, a magnetic disc, and an optical disc.

The image processor 126 reconstructs a cross-sectional image of the object 10 by using the acquired projection data set. The cross-sectional image may be a 3D image. In other words, the image processor 126 may reconstruct a 3D image of the object 10 by using a cone beam reconstruction method or the like, based on the acquired projection data set.

The interface 128 may receive an external input with respect to an X-ray tomography imaging condition, an image processing condition, or the like. For example, the X-ray tomography imaging condition may include tube voltages, an energy value setting with respect to a plurality of X-rays, a selection of an imaging protocol, a selection of an image reconstruction method, a setting of an FOV area, the number of slices, a slice thickness, a parameter setting with respect to image post-processing, or the like. Also, the image processing condition may include a resolution of an image, an attenuation coefficient setting for the image, setting for an image combining ratio, or the like.

The interface 128 includes a device for receiving a predetermined input from an external source. For example, the interface 128 may include a microphone, a keyboard, a mouse, a joystick, a touch pad, a touch pen, a voice recognition device, a gesture recognition device, or the like.

The display 130 displays an X-ray image reconstructed by the image processor 126.

Exchanges of data, power, and the like between the aforementioned elements may be performed by using at least one of wired communication, wireless communication, and optical communication.

The communication interface 132 may perform communication with an external device, an external medical apparatus, etc. via a server 134 or the like. The communication will be described with reference to FIG. 16.

Figure 3A:
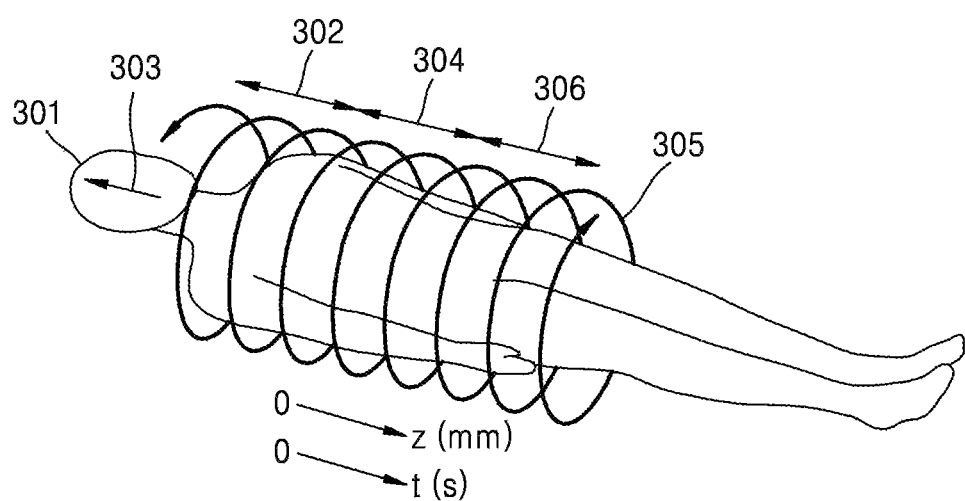
FIGS. 3A through 3C are diagrams showing processing of a medical image according to an exemplary embodiment.
Figure 3B:
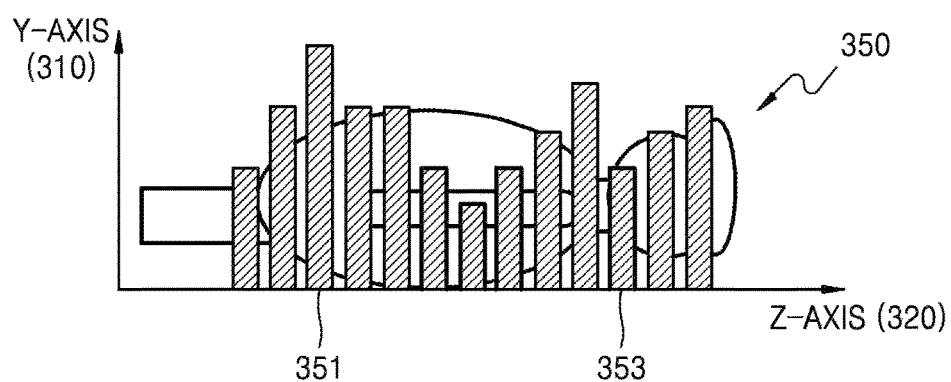
Figure 3C:
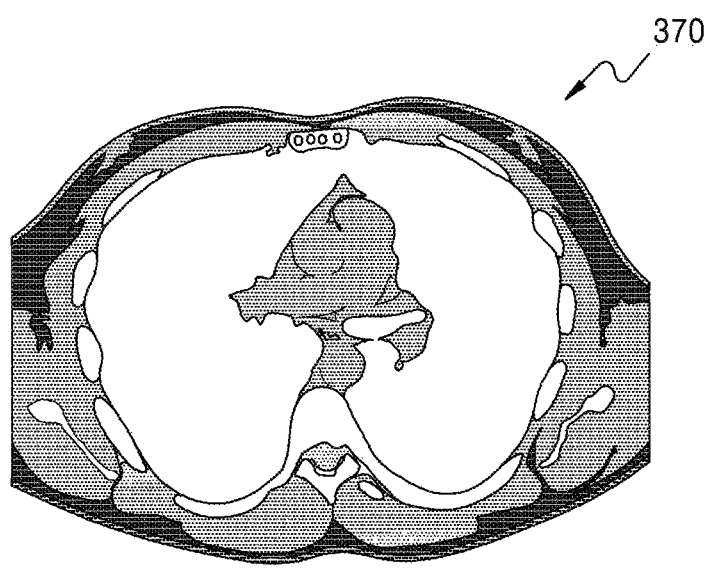

FIGS. 3A through 3C are diagrams showing processing of a tomography image according to an exemplary embodiment.

FIG. 3A shows an example where a tomography scan is performed using a helical scanning technique that is one among a number of scanning techniques that are used in tomography. Referring to FIG. 3A, the table (105 of FIG. 1) may move in an axial direction of an object 301, e. g., a z-axis direction 303. The X-ray generator (106 of FIG. 2) and the X-ray detector (108 of FIG. 2) rotate around the object 301 while the object 301 is moving due to movement of the table 105 in the z-axis direction 303. In this case, an X-ray light source of the X-ray generator (106 of FIG. 2) moves along a helical trajectory 305. Data acquired by the X-ray detector (108 of FIG. 2) along the helical trajectory 305 may be used to reconstruct a cross-sectional image.

Referring to FIG. 3A, the helical trajectory 305 may be divided into a plurality of first through third segments 302, 304, and 306. A cross-sectional image may be obtained using all data acquired along the plurality of segments 302, 304, and 306 of the helical trajectory 305. FIG. 3C shows an example of a cross-sectional image 370 that is reconstructed using pieces of data acquired along the helical trajectory 305.

Referring to FIG. 3A, pieces of data acquired along the first through third segments 302, 304, and 306 may correspond respectively to a plurality of body parts included in the object 301. The plurality of body parts may include organs such as the heart, lungs, stomach, liver, large intestine (or colon), small intestine, pelvis, brain, etc. Data acquired along the first segment 302 may correspond to the heart, lungs, etc. Data acquired along the second segment 304 may correspond to the liver and other body parts. Data acquired along the third segment 306 may correspond to the large intestine, small intestine, pelvis, etc.

Furthermore, although FIG. 3A shows an example of using a helical scanning technique, an axial scanning technique may be used to acquire data for reconstruction of a cross-sectional image.

FIG. 3B illustrates a graph 350 of a magnitude of a tube current corresponding to an amount of X-rays to which each body part of a patient is exposed during a tomography scan. An ordinate and an abscissa of the graph 350 may respectively represent a position along a direction that the table (105 of FIG. 1) moves, e. g., along a z-axis 320, and the magnitude of the tube current measured in milliamperes (mA). A tube current value along a y-axis 310 that is the ordinate may be a tube current (kilovolt-amps (KVA)) per rotation within the helical trajectory 305 shown in FIG. 3A. A volume, density, and penetration rate of X-rays may vary according to each body part being scanned. To acquire a cross-sectional image having a uniform resolution across body parts, a user may adjust the magnitude of the tube current differently along a direction of the z-axis 320 along which the patient moves. For example, on the z-axis 320 of the graph 350, the tube current is increased in a pelvis 351 having a relatively large volume among body parts, while a tube current is reduced in a neck 353 having a relatively small volume among the body parts.

To adjust a resolution of a cross-sectional image during a tomography scan in this way, an Automatic Exposure Control (AEC) technique may be used. If the AEC technique is used during a tomography scan, modulation of a tube current value may be automatically performed along at least one of the z-axis (320 of FIG. 3B) and the other two directions (x- and y-directions) perpendicular to the z-axis 320. According to the AEC technique, it is possible to acquire a cross-sectional image (370 of FIG. 3C) having a uniform resolution across body parts. In addition, the cross-sectional image 370 may depict a plurality of body parts at different resolutions, and only a minimum dose of X-rays may penetrate through a body part inside a body.

Figure 4A:
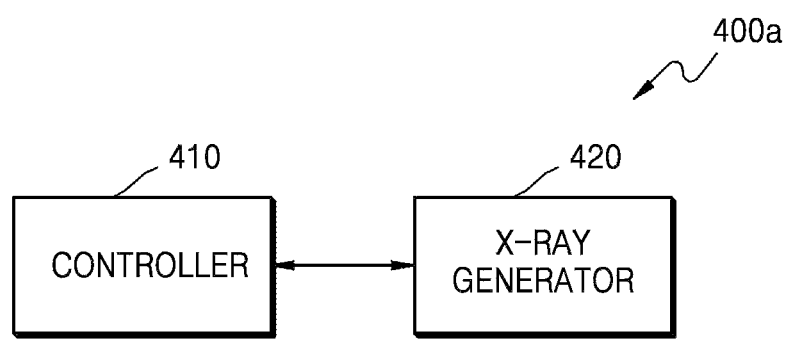
FIGS. 4A and 4B are block diagrams of medical image processing apparatuses according to exemplary embodiments.
Figure 4B:
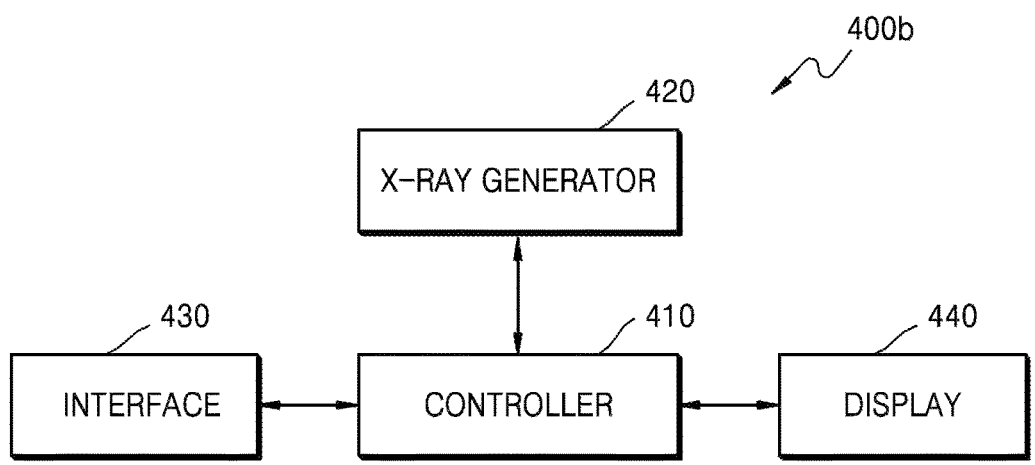

FIGS. 4A and 4B are block diagrams of medical image processing apparatuses 400a and 400b according to exemplary embodiments.

A medical image processing apparatus is an electronic device adapted to generate and process various types of medical images. In detail, the medical image processing apparatus is used to acquire an image showing an internal structure of an object. To do so, the medical image processing apparatus captures and/or processes images of details of structures, tissues, flow of fluid, etc., inside a body and provides the images to a user. The user, e.g., a medical practitioner, may use images output from the medical image processing apparatus to diagnose a patient's condition and diseases.

The medical image processing apparatus may be a magnetic resonance imaging (MRI) apparatus, a tomography apparatus, an X-ray apparatus, an ultrasound diagnosis apparatus, or the like, and may process at least one of an MRI image, a tomography image, an X-ray image, and an ultrasound image. It is assumed hereinafter that the medical image processing apparatus 400a or 400b is a tomography image processing apparatus for processing a tomography image.

Referring to FIG. 4A, the medical image processing apparatus 400a, i.e., the tomography image processing apparatus 400a generates a cross-sectional image of an object by transmitting X-rays through a first region of the object. The tomography image processing apparatus 400a includes a controller 410 and an X-ray generator 420.

In detail, the tomography image processing apparatus 400a may be any medical imaging apparatus that uses data acquired using radiation that has passed through an object to reconstruct an image. The tomography image processing apparatus 400a may be a computed tomography apparatus, an optical coherence tomography (OCT) apparatus, positron emission tomography (PET)-CT apparatus, or the like. Thus, tomography images acquired by the tomography image processing apparatus 400a may be a CT image, an OCT image, a PET image, or the like. In FIGS. 6A through 9, a tomography image is a CT image.

Referring to FIG. 4A, the tomography image processing apparatus 400a may be included in the CT system 100 described with reference to FIGS. 1 and 2. Furthermore, the tomography image processing apparatus 400a may be included in a medical apparatus or a portable device connected to the CT system 100 via a wireless or wired network, and accordingly, may be connected to the CT system 100 to be operated.

The first region is a region through which X-rays pass to create a cross-sectional image of the object, and may be predetermined by the user. If the user selects a body part to be examined, the first region including the selected body part may be automatically determined.

Figure 7:
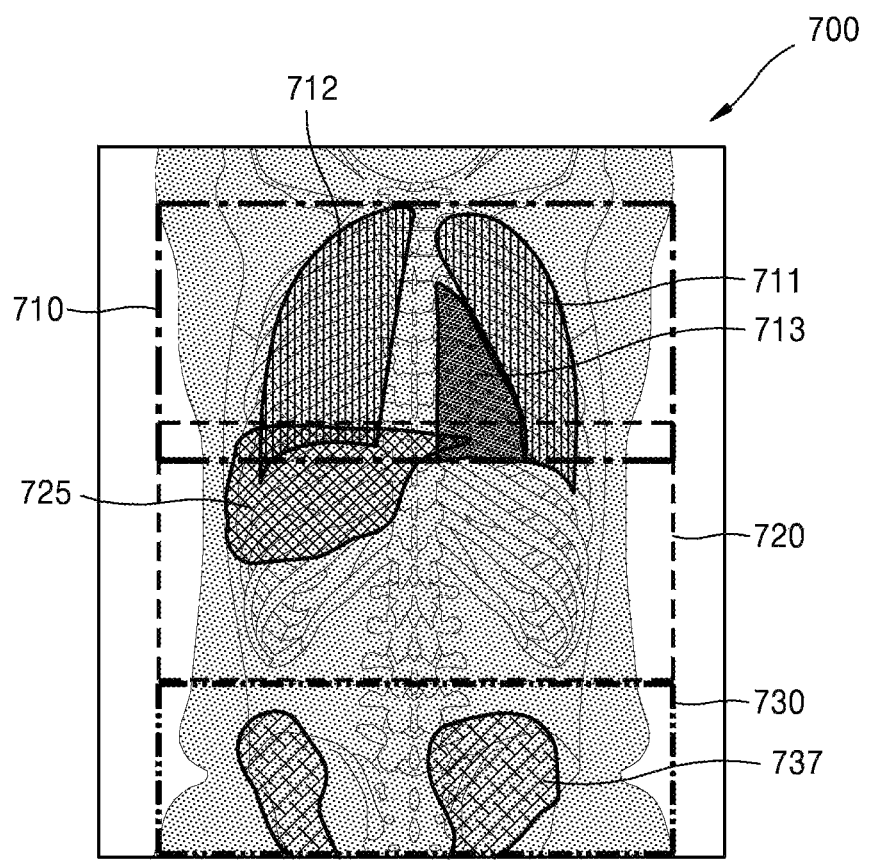
FIG. 7 is a scout image on which a plurality of sub-regions are indicated according to an exemplary embodiment.

The controller 410 determines a plurality of sub-regions included in the first region based on positions of a plurality of body parts included in the first region. FIG. 7 shows an example of a plurality of sub-regions 710, 720, and 730. The controller 410 determines a plurality of image qualities respectively corresponding to the plurality of sub-regions, based on respective types of the plurality of body parts included in the plurality of sub-regions.

Figure 8:
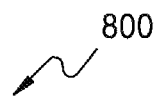
FIG. 8 is a priority table showing priorities and image quality indices assigned according to types of body parts, according to an exemplary embodiment.

The controller 410 may determine the plurality of image qualities based on priorities and image quality index values assigned to the respective types of the plurality of body parts. As shown in FIG. 8 illustrating a priority table 800, priorities and image quality index values assigned to respective types of body parts may be predetermined values.

First, an image quality index value may be determined based on a signal-to-noise ratio (SNR) of a cross-sectional image showing a body part to be examined. For example, if an SNR value has to be relatively low to diagnose a body part shown in a cross-sectional image, an image quality index value may be relatively small. If an SNR value is relatively high but does not prevent diagnosis of a body part shown in a cross-sectional image, an image quality index value may be relatively large.

Referring to FIG. 4A, the controller 410 may determine the plurality of image qualities according to the priorities determined based on the types of the plurality of body parts, as well as image quality index values. As shown in FIG. 7, if there is an overlapping portion between the sub-regions 710 and 720, priorities may be used to determine an image quality of each of the sub-regions 710 and 720. The priorities of the plurality of body parts may be priorities for diagnosis of the plurality of body parts included in a cross-sectional image. The priorities thereof may also be predetermined by the user. For example, the user may set a higher priority for a liver in a cross-sectional image including lungs and the liver, than for the lungs. The controller 410 controls X-rays whose doses are adjusted based on the plurality of image qualities, to pass through the object. The controller 410 may be included in the controller 118 shown in FIG. 2.

Referring to FIG. 4A, the X-ray generator 420 generates X-rays according to control by the controller 410, and emits the X-rays toward an object. The X-ray generator 420 may be included in the X-ray generator 106 of FIG. 2.

Referring to FIG. 4A, before a cross-sectional image is produced, the X-ray generator 420 may irradiate X-rays onto the object to generate a scout image. A scout image may be used to determine positions of a plurality of body parts. FIG. 6B shows a scout image 620 that is acquired before X-rays for generating a cross-sectional image are emitted. The scout image 620 may be obtained by emitting X-rays from the X-ray generator 420 that moves in the same direction as that in which the table (105 of FIG. 1) moves. The scout image 620 may be captured in advance using lower doses of X-rays than that for generating the cross-sectional image (370 of FIG. 3C). Positions of a plurality of body parts may be determined from the scout image 620 of FIG. 6B based on a reference image 610 of FIG. 6A in which positions of body parts have been set. A portion of a body in the scout image 620 may be segmented into the plurality of body parts based on the reference image 610 and then displayed, as described below in detail with reference to FIG. 6C.

Referring to FIGS. 1-2 and 4A, if the tomography image processing apparatus 400a is included in a medical apparatus or portable device connected to the CT system 100 via a wired or wireless network and is connected to the CT system 100 for its operation, the X-ray generator 420 may transmit a control signal for generating X-rays to the CT system 100 connected thereto. Thus, the X-ray generator 106 of the CT system 100 may allow intended X-rays to be irradiated onto the object, based on the control signal transmitted by the X-ray generator 420.

Referring to FIG. 4B, the tomography image processing apparatus 400b uses X-rays that penetrate through a first region of an object to generate a cross-sectional image of the object. Referring to FIG., 4B, the tomography image processing apparatus 400b includes the controller 410, the X-ray generator 420, an interface 430, and a display 440.

The tomography image processing apparatus 400b further includes the interface 430 and the display 440 in comparison to the tomography image processing apparatus 400a of FIG. 4A. Descriptions that are already provided above with respect to the controller 410 and the X-ray generator 420 shown in FIG. 4A are omitted.

Referring to FIG. 4B, the interface 430 receives a user input. The user input may include a user input for inputting priorities of a plurality of body parts. The user input may also include a user input for inputting image quality index values of the plurality of body parts. Furthermore, the user input may include a user input for selecting at least one among the plurality of body parts. The user input may be an input for selecting at least one among the plurality of body parts that are to be examined based on the scout image 620. For example, the user input may be an input for modifying positions of the plurality of body parts that are determined from the scout image 620 based on the reference image 610. The interface 430 shown in FIG. 4B may be included in the interface 128 shown in FIG. 2.

Referring to FIG. 4B, the display 440 may display a screen including at least one among a scout image and a cross-sectional image. The display 440 may display a scout image on which positions of a plurality of body parts are indicated. The display 440 may display a screen showing a dose of X-rays irradiated onto each of sub-regions. The display 440 may correspond to the display 130 shown in FIG. 2.

Figure 5:
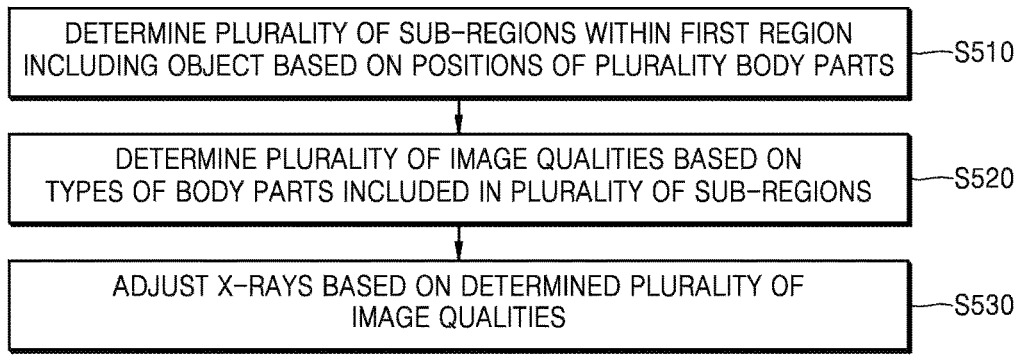
FIG. 5 is a flowchart of a method of processing a medical image according to an exemplary embodiment.

FIG. 5 is a flowchart of a method of processing a medical image according to an exemplary embodiment. The method may be performed by a medical image processing apparatus. It is assumed hereinafter that the medical image processing apparatus is a tomography image processing apparatus.

The tomography image processing apparatus 400a (400b) determines a plurality of sub-regions within a first region of an object, based on positions of a plurality of body parts (S510).

The tomography image processing apparatus 400a (400b) determines a plurality of image qualities based on types of the plurality of body parts included in the plurality of sub-regions (S520)

The tomography image processing apparatus 400a (400b) adjusts doses of X-rays that are irradiated onto the object based on the determined plurality of image qualities (S530).

A method of processing a medical image according to an exemplary embodiment will now be described in more detail with reference to FIGS. 6A through 9.

Figure 6A:
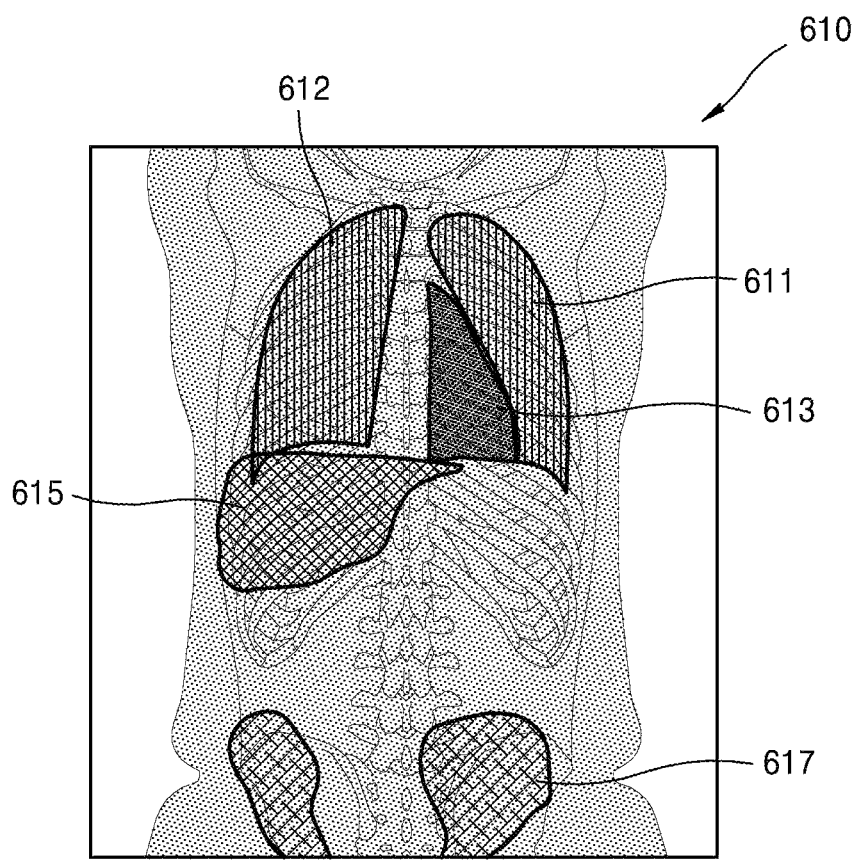
FIGS. 6A through 6C are a reference image and scout images, respectively, according to an exemplary embodiment.
Figure 6B:
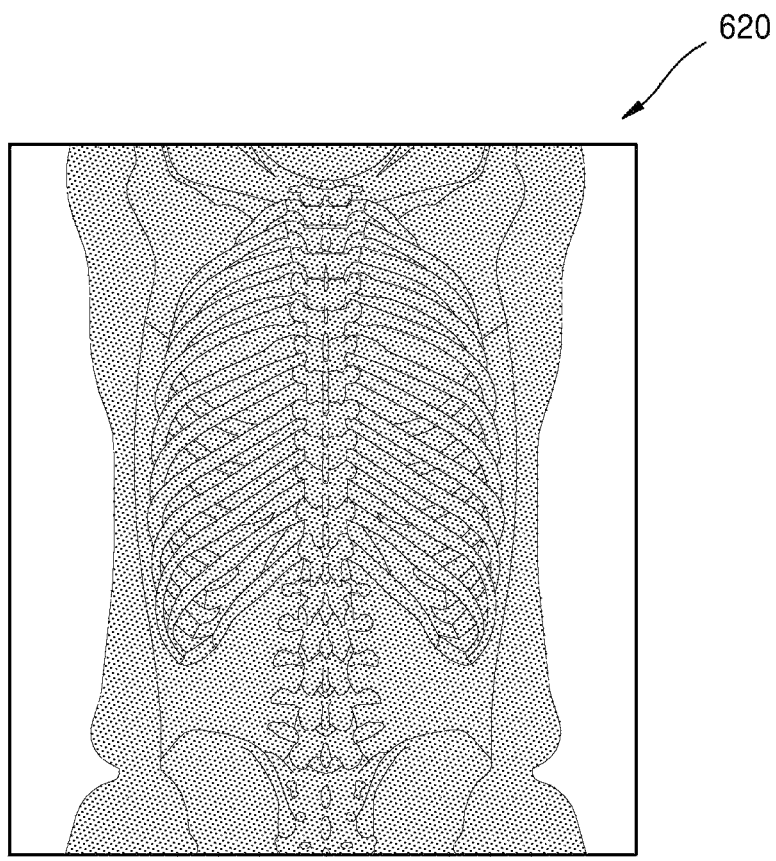
Figure 6C:
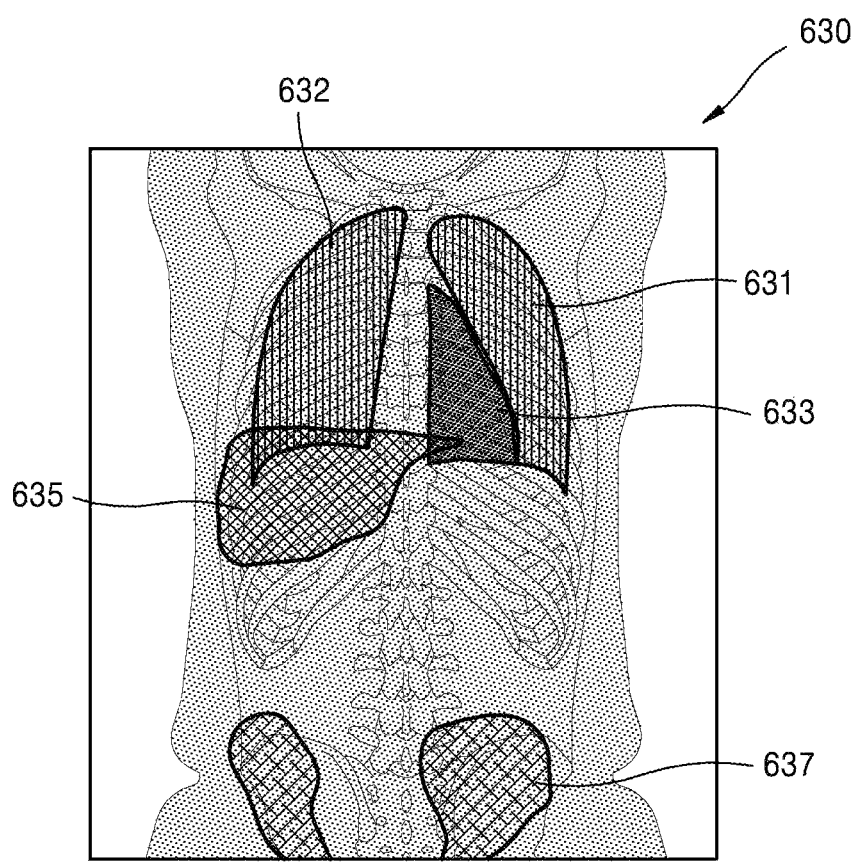

FIGS. 6A through 6C are a reference image and scout images, respectively, according to an exemplary embodiment.

The reference image 610 shown in FIG. 6A may be a reference image in which positions of a plurality of body parts have been set. The reference image 610 may be any medical image including all body parts to be scanned.

FIG. 6B shows an example where the scout image 620 is used as the reference image 610.

A scout image 630 shown in FIG. 6C is obtained by indicating positions of a plurality of body parts on the scout image 620 based on the reference image 610. For example, positions of lungs 631 and 632, a heart 633, a liver 635, and a pelvis 637 are indicated on the scout image 630. A portion of a body is segmented into the lungs 631 and 632, the heart 633, the liver 635, and the pelvis 637 based on positions of their counterparts, i.e., lungs 611 and 612, a heart 613, a liver 615, and a pelvis 617 in the reference image 610 of FIG. 6A, and positions of the lungs 631 and 632, the heart 633, the liver 635, and the pelvis 637 are indicated on the scout image 630. The indicated positions may be modified by a user.

The user may select at least one body part to be depicted in a cross-sectional image among a plurality of body parts whose positions have been indicated. For example, the user may select the lungs 631 and 632, the heart 633, the liver 635, and the pelvis 637 from the scout image 630. The tomography image processing apparatus 400a (400b) allows X-rays to pass through a first region including the lungs 631 and 632, the heart 633, the liver 635, and the pelvis 637, thereby generating a cross-sectional image.

FIG. 7 is a scout image 700 on which a plurality of sub-regions are indicated according to an exemplary embodiment. The plurality of sub-regions includes the first through third sub-regions 710, 720, and 730. The first through third sub-regions 710, 720, and 730 are determined based on positions of a plurality of body parts selected from the scout image 700. For example, the selected plurality of body parts is lungs 711 and 712, a heart 713, a liver 725, and a pelvis 737. The first sub-region 710 includes the lungs 711 and 712 and the heart 713, the second sub-region 720 includes the liver 725, and the third sub-region 730 includes the pelvis 737. The controller 410 may determine a plurality of image qualities respectively corresponding to the first through third sub-regions 710, 720, and 730, based on types of the plurality of body parts included in the first through third sub-regions 710, 720, and 730.

FIG. 8 is priority table 800 showing priorities and image quality indices assigned according to types of body parts, according to an exemplary embodiment. As illustrated in the priority table 800, for example, the priorities of the body parts increase in an order from a liver to a pelvis to lungs to a brain. An image quality index of a body part may be determined based on an SNR of a cross-sectional image showing the body part included in each of a plurality of sub-regions. Furthermore, the image quality index of a body part may be determined based on at least one among a density and a volume of the body part. For example, image quality indices of the liver, pelvis, lungs, and brain are 15, 18, 25, and 10, respectively. The pelvis and the lungs have high image quality indices because they have more empty spaces in tissues thereof than the liver and the brain. In other words, due to their high image quality indices, lesions in the pelvis and lungs may be diagnosed even using a cross-sectional image having a high SNR value.

Figure 9:
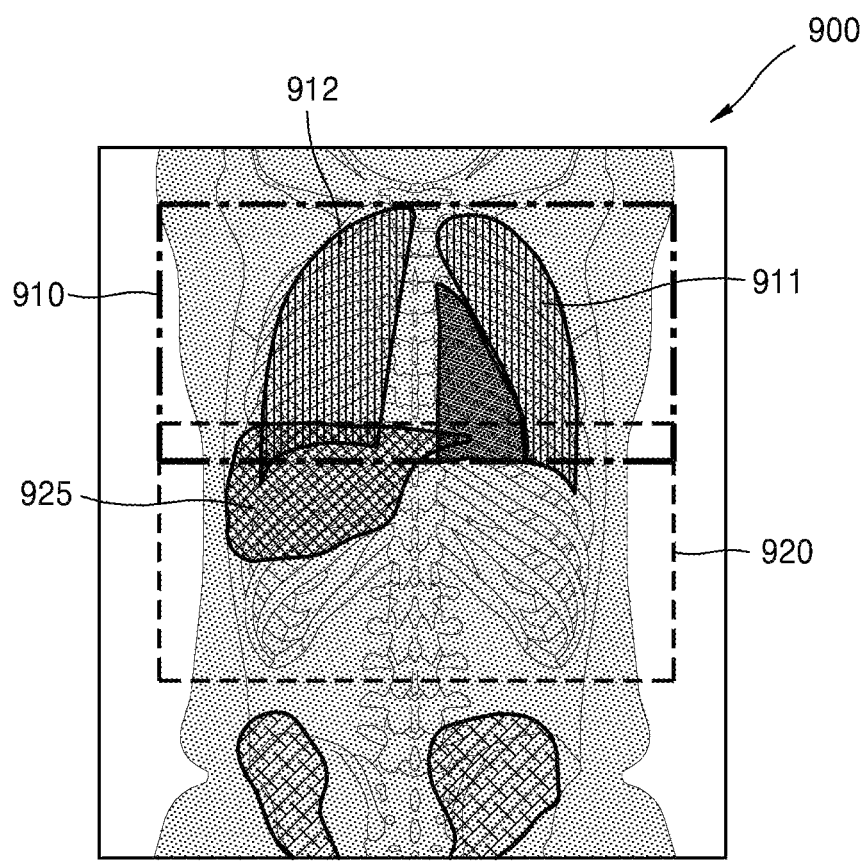
FIGS. 9 and 10 are screens according to an exemplary embodiment.
Figure 10:
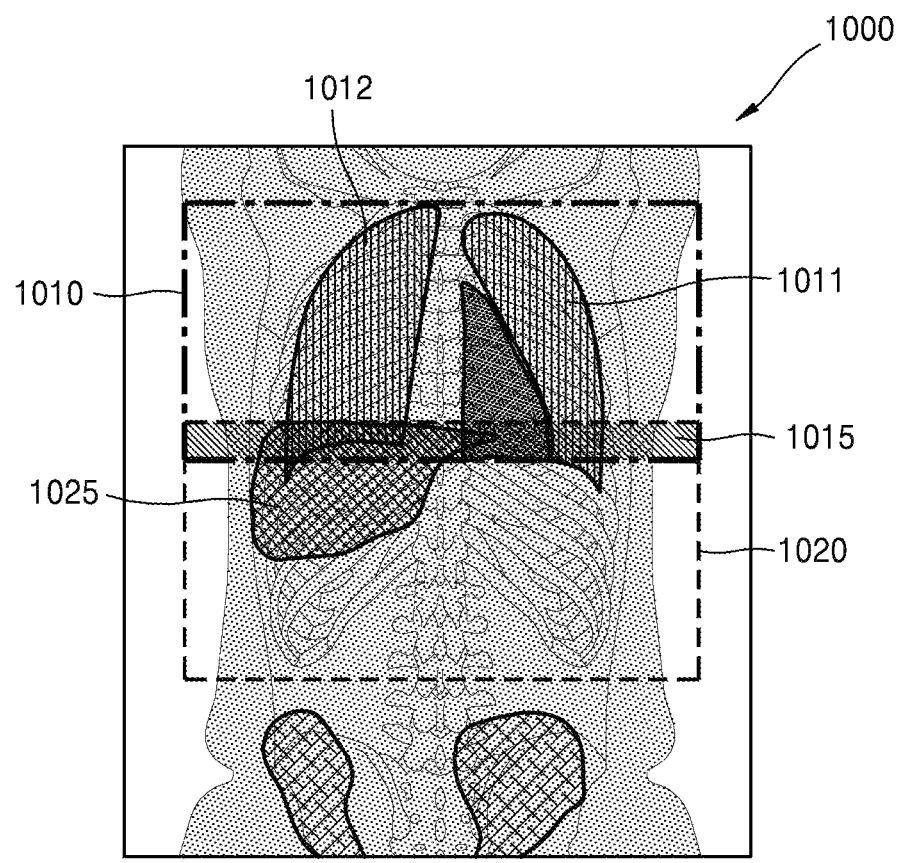

FIGS. 9 and 10 are screens according to an exemplary embodiment.

Referring to FIG. 9, first and second sub-regions 910 and 920 are shown in a scout image 900.

A user may select a plurality of body parts to be depicted in a cross-sectional image. The controller 410 may determine a region of an object to which X-rays are irradiated, based on the plurality of body parts selected via a user input. For example, lungs 911 and 912 and a liver 925 may be selected via a user input, and X-rays may be irradiated only onto the first and second sub-regions 910 and 920 determined based on positions of the lungs 911 and 912 and the liver 925.

According to an exemplary embodiment, it is possible to vary doses of X-rays being irradiated onto the first sub-region 910 including the lungs 911 and 912 among a plurality of body parts and the second sub-region 920 including the liver 925 among the plurality of body parts, based on priorities and image quality indices of the first and second sub-regions 910 and 920. For example, a smaller dose of X-rays may be irradiated on the lungs having a higher image quality index value than on the liver. Varying doses of X-rays according to types of a plurality of body parts may reduce an amount of X-rays to which the human body is exposed, as compared to representation of the plurality of body parts at the same image quality level.

Referring to FIG. 10, first and second regions 1010 and 1020 and an overlapping region 1015 between the first and second regions 1010 and 1020 are shown in a scout image 1000.

The overlapping region 1015 between the first and second regions 1010 and 1020 may correspond to an overlapping portion between the first and second sub-regions 910 and 920. A sum of the first region 1010 and the overlapping region 1015 may correspond to the first sub-region 910 shown in FIG. 9. A sum of the second region 1020 and the overlapping region 1015 may correspond to the second sub-region 920 shown in FIG. 9.

Lungs 1011 and 1012 and a liver 1025 may be selected from the scout image 1000 via a user input. Because the lungs 1011 and 1012 and the liver 1025 overlap each other in the scout image 1000, the overlapping region 1015 exists between first and second sub-regions 1010 and 1020 (the first and second sub-regions 910 and 920 of FIG. 9) determined based on the selected lungs 1011 and 1012 and the liver 1025. An image quality of the overlapping region 1015 may correspond to an image quality index value of a body part having a higher priority among body parts included in the first and second sub-regions 910 and 920. For example, as illustrated in the priority table 800 of FIG. 8, because the liver 1025 has a higher priority than the lungs 1011 and 1012, the image quality of the overlapping region 1015 may be determined based on an image quality index value (e. g., 15) of the liver 1025.

An image quality corresponding to the first region 1010 may be determined based on an image quality index value (e. g., 25) of the lungs 1011 and 1012. An image quality corresponding to the second region 1020 and the overlapping region 1015 may be determined based on the image quality index value (e.g., 15) of the liver 1025.

For each of the first region 1010, the second region 1020, and the overlapping region 1015, a dose of X-rays corresponding to the determined image quality thereof may be determined. In detail, a different dose of X-rays is irradiated on each of the first region 1010, the second region 1020, and the overlapping region 1015 by applying a different tube current (KVA) per rotation thereto. Doses of X-rays that are irradiated onto sub-regions may be varied based on respective priorities and image quality index values. Furthermore, X-rays may be irradiated on a region where a plurality of organs overlap each other according to a priority, thereby reducing a dose of X-rays to which an organ is exposed while maintaining an appropriate image quality level of a cross-sectional image.

According to another exemplary embodiment, it is possible to determine a tube current value per rotation so that the tube current value does not change abruptly but steadily at a region where the first region 1010 and the overlapping region 1015 contact each other. Similarly, a tube current value per rotation may also be determined to steadily change at a region where the overlapping region 1015 and the second region 1020 contact each other.

According to exemplary embodiments, it is possible to acquire a cross-sectional image that smoothly depicts a portion corresponding to a boundary between regions having different image qualities.

The display 440 may display a screen showing a dose of X-rays being irradiated on each of sub-regions, e. g., a tube current value per rotation.

Figure 11:
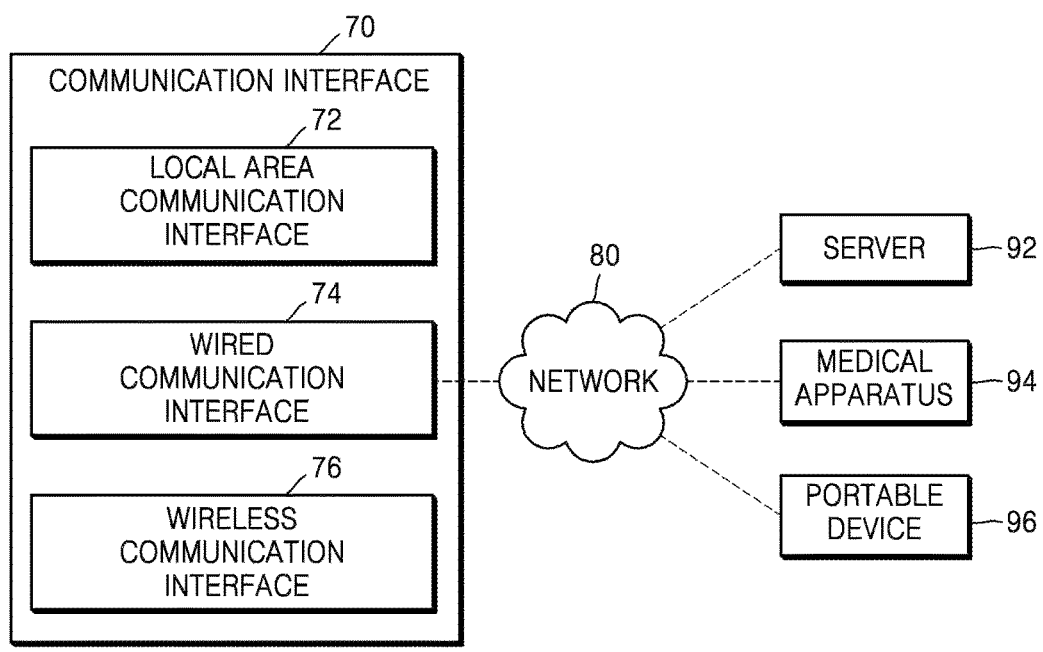
FIG. 11 is a schematic diagram of a communication interface according to an exemplary embodiment.

FIG. 11 is a schematic diagram of a communication interface 70 according to an exemplary embodiment. The communication interface 70 may transmit and receive data to and from a hospital server or another medical apparatus in a hospital, which is connected through a picture archiving and communication system (PACS), and perform data communication according to the digital imaging and communications in medicine (DICOM) standard.

As shown in FIG. 11, the communication interface 70 is connected to a network 80 by wire or wirelessly to communicate with a server 92, a medical apparatus 94, and a portable device 96.

In detail, the communication interface 70 may transmit and receive data related to a diagnosis of an object through the network 80, and may also transmit and receive a medical image captured by the medical apparatus 94, such as a CT apparatus, an MRI apparatus, or an X-ray apparatus. In addition, the communication interface 70 may receive a diagnosis history or a treatment schedule of the object from the server 92, and use the same to diagnose the object. The communication interface 70 may perform data communication not only with the server 92 or the medical apparatus 94 in a hospital, but also with the portable device 96, such as a mobile phone, a personal digital assistant (PDA), or a laptop of a doctor or customer.

Also, the communication interface 70 may transmit information about a malfunction of the CT system or about a medical image quality to a user through the network 80, and receive a feedback regarding the information from the user.

The communication interface 70 may include at least one component enabling communication with an external apparatus. For example, the communication interface 70 includes a local area communication interface 72, a wired communication interface 74, and a wireless communication interface 76.

The local area communication interface 72 refers to a interface for performing local area communication with an apparatus within a predetermined distance. Examples of local area communication technology include, but are not limited to, a wireless local area network (LAN), Wi-Fi, Bluetooth, ZigBee, Wi-Fi direct (WFD), ultra wideband (UWB), infrared data association (IrDA), Bluetooth low energy (BLE), and near field communication (NFC).

The wired communication interface 74 refers to a interface for performing communication by using an electric signal or an optical signal. Examples of wired communication technology include wired communication techniques using a twisted pair cable, a coaxial cable, and an optical fiber cable, and other well known wired communication techniques.

The wireless communication interface 76 transmits and receives a wireless signal to and from at least one among a base station, an external apparatus, and a server in a mobile communication network. Here, the wireless signal may be a voice call signal, a video call signal, or data in any one of various formats according to transmission and reception of a text/multimedia message.

The tomography image processing apparatuses 400a and 400b of FIGS. 4A and 4B may be the external medical apparatus 94 or portable device 96 connected to the network 80. In other words, the tomography image processing apparatuses 400a and 400b may be connected to the communication interface 70 shown in FIG. 11 to be operated.

In addition, the exemplary embodiments may also be implemented through computer-readable code and/or instructions on a medium, e.g., a non-transitory computer-readable medium, to control at least one processing element to implement any above-described embodiments. The medium may correspond to any medium or media which may serve as a storage and/or perform transmission of the computer-readable code.

The computer-readable code may be recorded and/or transferred on a medium in a variety of ways, and examples of the medium include recording media, such as magnetic storage media (e.g., ROM, floppy disks, hard disks, etc.) and optical recording media (e.g., compact disc read only memories (CD-ROMs) or digital versatile discs (DVDs)), and transmission media such as Internet transmission media. Thus, the medium may have a structure suitable for storing or carrying a signal or information, such as a device carrying a bitstream according to one or more exemplary embodiments. The medium may also be on a distributed network, so that the computer-readable code is stored and/or transferred on the medium and executed in a distributed fashion. Furthermore, the processing element may include a processor or a computer processor, and the processing element may be distributed and/or included in a single device.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A medical image processing apparatus comprising:
an X-ray generator configured to generate X rays; and
a controller configured to:
  determine sub-regions included in a region of an object, based on positions of body parts included in the region;
  determine image qualities of the sub-regions based on types of the body parts included in the sub-regions;
  control doses of the X-rays based on the image qualities;
  control the X-ray generator to transmit the controlled X-rays to the region; and
  generate a cross-sectional image of the object by transmitting the X-rays through the region of the object,
wherein the controller is further configured to, in response to the sub-regions overlapping each other, determine an image quality of an overlapping region between the sub-regions based on priorities of the body parts.

2. The apparatus of claim 1, wherein the image qualities comprise image quality indices of the body parts, and
each of the image quality indices is determined based on a signal-to-noise ratio of a cross-sectional image showing a respective one of the body parts.

3. The apparatus of claim 1, further comprising an interface configured to receive an input of priorities and/or image quality indices of the body parts.

4. The apparatus of claim 1, wherein the image qualities comprise image quality indices of the body parts, and
each of the image quality indices is determined based on a density and/or a volume of a respective one of the body parts.

5. The apparatus of claim 1, wherein the X-ray generator is further configured to transmit the X-rays through the object to generate a scout image for determining the positions of the body parts.

6. The apparatus of claim 5, further comprising a display configured to display the scout image and/or the cross-sectional image.

7. The apparatus of claim 6, wherein the display is further configured to display the scout image on which the positions of the body parts are indicated.

8. The apparatus of claim 7, wherein the scout image on which the positions of the body parts are indicated is generated based on a reference image on which the positions of body parts are set.

9. The apparatus of claim 7, further comprising an interface configured to receive an input for modifying the positions of the body parts that are indicated on the scout image.

10. The apparatus of claim 1, further comprising an interface configured to receive an input for selecting the body parts.

11. The apparatus of claim 10, wherein the controller is further configured to determine another region of the object to which the X-rays are transmitted, based on the selected body parts.

12. The apparatus of claim 1, wherein the controller is further configured to control the doses of the X-rays that are transmitted to the respective sub-regions, based on the image qualities.

13. The apparatus of claim 1, further comprising a display configured to display the controlled doses of the X-rays that are transmitted to the respective sub-regions.

14. The apparatus of claim 1, wherein the medical image processing apparatus is a tomography apparatus, and
the controller is further configured to control a tube current per rotation of each of the X-rays that are transmitted to the respective sub-regions, based on the image qualities.

15. A medical image processing method comprising:
generating X-rays;
determining sub-regions included in a region of an object, based on positions of body parts included in the region;
determining image qualities of the sub-regions based on types of the body parts included in the sub-regions;
controlling doses of the X-rays based on the image qualities;
transmitting the controlled X-rays to the region; and
generating a cross-sectional image of the object by transmitting the X-rays through the region of the object,
wherein the determining the image qualities comprises, in response to the sub-regions overlapping each other, determining an image quality of an overlapping region between the sub-regions based on priorities of the body parts.

16. The method of claim 15, wherein the controlling the doses of the X-rays comprises controlling the doses of the X-rays that are transmitted to the respective sub-regions, based on the image qualities.

17. The method of claim 15, further comprising displaying the controlled doses of the X-rays that are transmitted to the respective sub-regions.

18. A computer program product comprising a computer readable storage medium having a computer readable program stored therein, wherein the computer readable program, when executed on a computing device, causes the computing device to:
  determine a region of an object, the region comprising a body part;
  determine an image quality of the region based on a type of the body part;
  control a X-ray generator to transmit a dose of an X-ray to the region based on the image quality; and
  generate a cross-sectional image of the object by transmitting X-rays through the region of the object,
wherein the computing device is further configured to, in response to sub-regions included in the region overlapping each other, determine an image quality of an overlapping region between the sub-regions based on priorities of the body parts.

19. The computer program product of claim 18, wherein the computing device is further configured to:
  determine a priority and/or an index of the region based on a table comprising the type of the body part corresponding to the priority and/or the index; and
  control the X-ray generator to transmit a tube current per rotation of the X-ray to the region based on the priority and/or the index.

20. The computer program product of claim 18, wherein the computing device is further configured to:
  control to generate another X-ray;
  determine another region of the object, the other region comprising another body part;
  determine another image quality of the other region based on another type of the other body part; and control the X-ray generator to transmit another dose of the other X-ray to the other region based on the other image quality.

\* \* \* \* \*